US00PP26953P3

(12) United States Plant Patent
Zaiger et al.

(10) Patent No.: US PP26,953 P3
(45) Date of Patent: Jul. 19, 2016

(54) INTERSPECIFIC TREE NAMED 'ZOEY KAT'

(50) Latin Name: **Interspecific *Prunus* species**
Varietal Denomination: Zoey Kat

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 89 days.

(21) Appl. No.: 14/544,059

(22) Filed: Nov. 21, 2014

(65) Prior Publication Data

US 2016/0150700 P1 May 26, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit with good flavor and eating quality.
4. Fruit with an average Brix of 17.0°.
5. Fruit with an attractive dark reddish blue skin color and yellow flesh.

1 Drawing Sheet

Botanical designation: Interspecific *Prunus* species.
Variety denomination: 'Zoey Kat'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific and apricot trees, which are known to us, and mentioned herein is, 'Flavor Jewel' Interspecific (U.S. Plant Pat. No. 13,502) and our non-patented interspecific seedling selections with the field identification numbers '192LD95', '53ZB678', '65LG172', '47GH333A', '305LN566' and '67Z80'.

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species; *Prunus salicina,*

*Prunus armeniaca* and *Prunus persica*. The present variety was selected from a first generation cross between our proprietary non-patented interspecific varieties '53ZB678' and '305LN566'. The non-patented interspecific seed parent (53ZB678) originated from a cross between '65LG172' interspecific (non-patented) and the proprietary non-patented interspecific variety '47GH333A'. The non-patented interspecific pollen parent (305LN566) originated from a cross between the non-patented proprietary interspecific variety '192LD95' and the non-patented proprietary interspecific variety '67Z80'. A large number of these first generation seedlings were budded onto older established trees of 'Nemaguard' Rootstock (non-patented) to enhance earlier fruit production for evaluation. Under close and careful observation we recognized the desirable tree and fruit characteristics of the present seedling and selected it in 2005 for additional asexual propagation and commercialization.

ASEXUAL REPRODUCTION OF THE VARIETY

In 2005 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree [Plum×apricot×(apricot×peach)] is of large size, vigorous, upright growth and is a regular and productive bearer of large size, yellow flesh fruit with good flavor and eating quality. The fruit is further characterized by having firm flesh and an attractive reddish blue skin color. In comparison to its non-patented interspecific seed parent (53ZB678) the fruit of the new variety has a higher average Brix of 17.0° and is approximately 28 days earlier in maturity. In comparison to its non-patented proprietary interspecific pollen parent (305LN566) the fruit of the new variety is larger in size and is approximately 13 days earlier in maturity. In comparison to the commercial variety 'Flavor Jewel' Interspecific (U.S. Plant Pat. No. 13,502) the fruit of the new variety has dark reddish blue skin compared to red and is approximately 61 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 9 year old specimens grown near Modesto, Calif., with color in accordance with Munsell Book of Color published in 1958.

Tree:

*Size.*—Large, pruned to 3 to 3.5 meters in height and width for economical harvesting of fruit. Varies with different cultural practices.

*Vigor.*—Vigorous, tree growth of 1.5 to 2 meters the first growing season. Varies with cultural practices, soil type, fertility and climatic conditions.

*Form.*—Upright growth, usually pruned to vase shape.

*Branching habit.*—Upright, crotch angle approximately 30°, increases with heavy crop load.

*Productivity.*—Productive, thinning and spacing of fruit necessary for marketable size fruit. Number of fruit set varies with climatic conditions during blooming period.

*Bearer.*—Regular, adequate fruit set 7 consecutive years. No alternate bearing observed.

*Fertility.*—Self-sterile, pollinator required.

*Density.*—Medium dense, usually pruned to vase shape to increase air movement and sunlight to enhance fruit color and health of fruit spurs.

*Hardiness.*—Hardy in all stone fruit growing areas of California. Tree grown in USDA Hardiness Zone 9. Winter chilling requirement is approximately 800 hours at or below 45° F.

Trunk:

*Size.*—Large. Average circumference 48.3 cm, at 22.9 cm above ground on a 9 year old tree.

*Stocky.*—Medium stocky.

*Texture.*—Medium shaggy, roughness increases with age.

*Color.*—Varies from 2.5Y 2/2 to 5Y 4/2.

Branches:

*Size.*—Medium. Average circumference 16.8 cm at 1.2 meters above ground. Crotch angle approximately 30°, increases with heavy crop load.

*Surface texture.*—New growth relatively smooth. Mature growth medium rough, roughness increases with age.

*Lenticels.*—Size — large. Average number 48 in a 25.8 sq cm section. Average length 5.4 mm. Average width 2.0 mm. Color varies from 5YR 5/12 to 7.5YR 5/10.

*Color.*—New growth varies from 2.5GY 6/8 to 2.5GY 5/6. Mature growth varies from 7.5YR 6/2 to 7.5YR 2/2, varies with age of growth.

Leaves:

*Size.*—Medium to large. Average length 120.2 mm. Average width 49.3 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins. Lower surface relatively smooth except for small ridges created by midrib and pinnate venation. Both upper and lower surfaces glabrous.

*Petiole.*—Medium to large. Average length 15.7 mm. Average width 1.7 mm. Longitudinally grooved. Surface — finely pubescent. Color varies from 2.5GY 5/6 to 2.5GY 5/8.

*Glands.*—Type — globose. Number varies from 2 to 3, average number 2. Size — small. Average length 0.8 mm. Average diameter 0.6 mm. Located primarily on base of leaf blade and upper portion of petiole. Color varies from 2.5GY 5/6 to 2.5GY 5/8.

*Stipules.*—Average number 2. Average length 6.1 mm. Edges — pectinate. Color varies from 2.5GY 6/6 to 2.5GY 6/8.

*Color.*—Upper surface varies from 5GY 3/6 to 7.5GY 3/6. Lower surface varies from 5GY 4/6 to 5GY 3/4. Midvein color varies from 2.5GY 5/6 to 5GY 5/8.

Flower buds:

*Size.*—Medium. Average length 9.7 mm. Average diameter 8.9 mm.

*Hardiness.*—Hardy with respect to California winters.

*Form.*—Conical, becoming elongated just before opening.

*Pedicel.*—Average length 7.5 mm. Average width 0.8 mm. Color varies from 2.5GY 6/8 to 5GY 7/8. Surface glabrous.

*Color.*—N 9.5/ (white).

*Number of buds per spur.*—Average number 7, varies from 4 to 13. Varies with age of spur.

*Density.*—Medium dense.

Flowers:

*Blooming period.*—Date of First Bloom Feb. 12, 2014. Date of Petal Fall Feb. 22, 2014, varies slightly with climatic conditions.

*Size.*—Medium. Average height 11.7 mm. Average diameter 15.5 mm.

*Petals.*—Number — normally 5, alternately arranged to sepals. Petal apex — rounded. Petal base — rounded to somewhat truncated. Size — medium. Average length 8.8 mm. Average width 7.1 mm. Form — globose to elliptical. Arrangement — overlapping. Margin — sinuate. Color N 9.5/(white). Both upper and lower surfaces glabrous.

*Sepals.*—Number — normally 5, alternately arranged to petals. Size — small. Average length 2.8 mm. Average width 2.0 mm. Shape — triangular. Apex rounded to triangular. Margin — entire. Color — upper surface varies from 5GY 6/8 to 7.5GY 6/8. Lower surface varies from 5GY 6/6 to 5GY 6/8. Both upper and lower surfaces glabrous.

*Stamens.*—Average number per flower 32, varies from 29 to 34. Average filament length 8.1 mm. On average the stamens are above the height of the petals. Filament color N 9.5/(white). Anther color varies from 5Y 8/8 to 5Y 8/10.

*Pollen.*—Self-sterile, pollinator required. Color varies from 5Y 7/10 to 5Y 7/12.

*Pistil.*—Number — normally 1. Surface — glabrous. Average length 8.7 mm. Position of stigma an average of 1.5 mm below anthers. Color varies from 10Y 7/8 to 2.5GY 8/6.

*Fragrance.*—Heavy aroma.

*Color.*—N 9.5/(white).

*Pedicel.*—Average length 9.8 mm. Average width 0.8 mm. Color varies from 2.5GY 6/8 to 5GY 7/8. Surface glabrous.

*Number flowers per flower bud.*—Average number 2, varies from 2 to 3.

Fruit:

*Maturity when described.*—Firm ripe and ready for consumption.

*Date of first picking.*—Aug. 4, 2014.

*Date of last picking.*—Aug. 14, 2014, varies slightly with climatic conditions.

*Size.*—Large. Average diameter axially 56.0 mm. Average transversely in suture plane 65.1 mm. Average weight 156.2 grams, varies slightly with fertility of the soil, amount of thinning and climatic conditions.

*Form.*—Globose.

*Suture.*—Lipped, extends from base to apex.

*Ventral surface.*—Slightly lipped.

*Apex.*—Slightly retuse.

*Base.*—Flat.

*Stem cavity.*—Rounded to slightly elongated in suture plane. Average depth 7.0 mm. Average diameter 2.7 mm.

Stem:

*Size.*—Medium. Average length 14.0 mm. Average diameter 1.6 mm.

*Color.*—Varies from 7.5YR 4/6 to 10YR 4/4.

Flesh:

*Ripens.*—Evenly.

*Texture.*—Firm, meaty.

*Fibers.*—Few, small, tender.

*Firmness.*—Firm, comparable to commercial interspecific varieties.

*Aroma.*—Moderate.

*Amydgalin.*—Undetected.

*Eating quality.*—Good.

*Flavor.*—Good with a good balance between acid and sugar.

*Juice.*—Moderate amount, enhances flavor.

*Acidity.*—Not available.

*Brix.*—Average Brix 17.0°, varies slightly with amount of fruit per tree and climatic conditions.

*Color.*—Varies from 2.5Y 7/8 to 2.5Y 8/8.

*Pit cavity.*—Average length 26.4 mm. Average width 21.4 mm. Average depth 6.4 mm. Color varies from 7.5YR 5/8 to 7.5YR 4/8.

Skin:

*Thickness.*—Medium.

*Surface.*—Smooth.

*Bloom.*—Slight amount, completely covered.

*Tendency to crack.*—None.

*Color.*—Ground color varies from 7.5YR 9/2 to 10YR 9/2. Overspread with 7.5R 3/10 to 7.5R 2/6.

*Tenacity.*—Tenacious to flesh.

*Astringency.*—Undetected.

Stone:

*Type.*—Clingstone, medium adherence.

*Size.*—Medium to large. Average length 25.4 mm. Average width 20.4 mm. Average thickness 10.8 mm.

*Form.*—Obovoid.

*Base.*—Flat.

*Apex.*—Pointed. Average length 1.8 mm.

*Surface.*—Pitted throughout, pits vary from rounded to slightly elongated.

*Sides.*—Unequal, one side extending further from the suture plane.

*Ridges.*—A small ridge on each side of suture extending from base to apex.

*Tendency to split.*—None.

*Color.*—Varies from 7.5YR 5/6 to 7.5YR 6/6 when dry.

Kernel:

*Size.*—Small to medium. Average length 12.2 mm. Average width 9.4 mm. Average depth 4.7 mm.

*Form.*—Ovate.

*Viability.*—Viable, complete embryo development.

*Skin color.*—Varies from 7.5YR 5/8 to 7.5YR 6/8.

Use: Dessert.

*Market.*—Local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

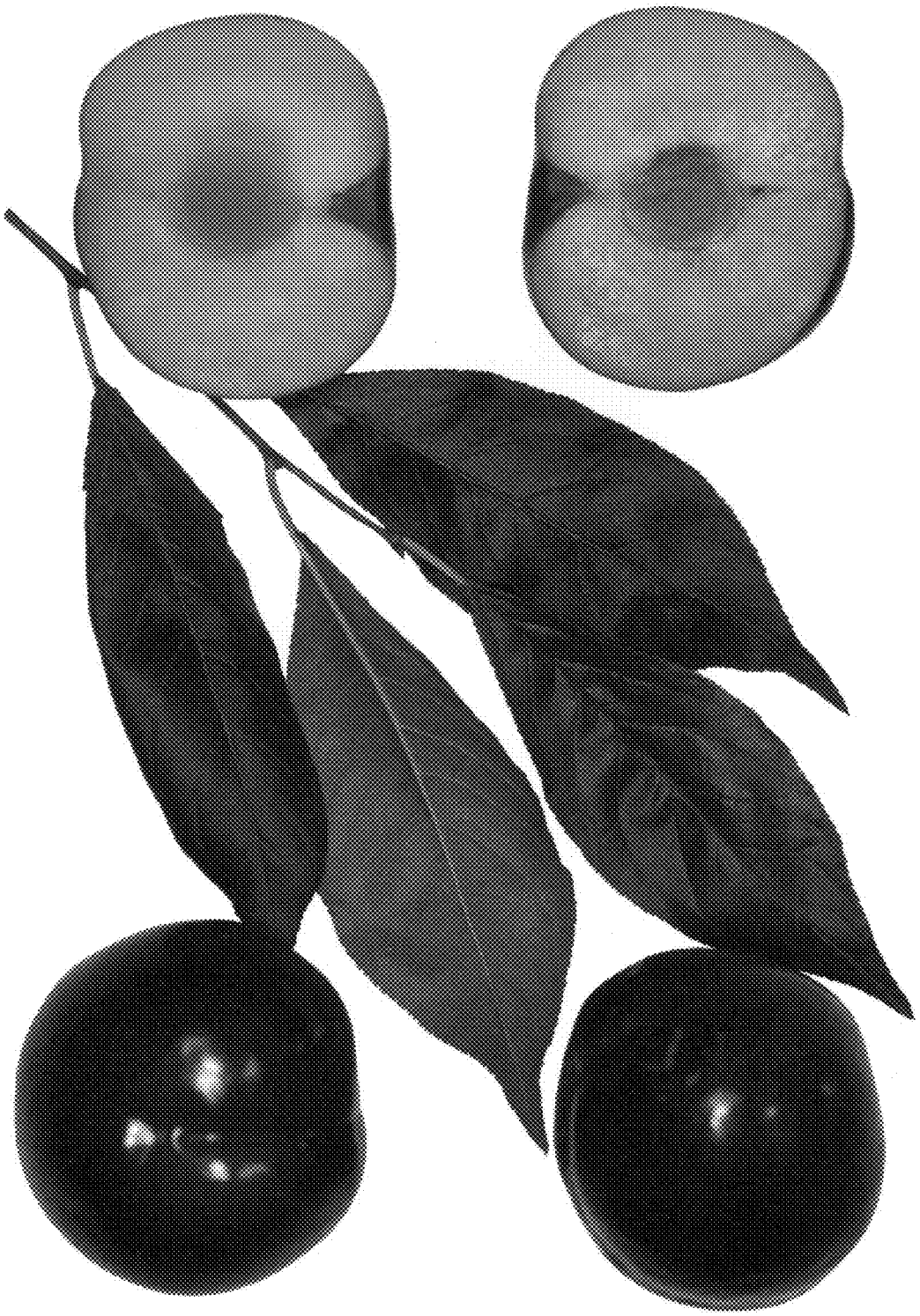

* * * * *